United States Patent [19]

Cain

[11] 4,003,246
[45] Jan. 18, 1977

[54] SPECIMEN CRACK STRESS INTENSITY CONTROL LOOP FOR TEST DEVICE

[75] Inventor: Patrick J. Cain, Eden Prairie, Minn.

[73] Assignee: MTS Systems Corporation, Minneapolis, Minn.

[22] Filed: Aug. 8, 1975

[21] Appl. No.: 603,134

[52] U.S. Cl. .................................. 73/90; 73/91
[51] Int. Cl.² .................................. G01N 3/32
[58] Field of Search ........... 73/95, 90, 91, 89, 88 R

[56] References Cited
UNITED STATES PATENTS

| 3,918,299 | 11/1975 | Donnadieu | 73/91 |
| R26,782 | 2/1970 | Preston | 73/90 |

OTHER PUBLICATIONS

Reuter et al., In-Test Crack-Opening-Displacement Calibration, Engineering Fracture Mech. (1972), vol. 4, pp. 183-188.

*Primary Examiner*—James J. Gill
*Assistant Examiner*—Anthony V. Ciarlante
*Attorney, Agent, or Firm*—Dugger, Johnson & Westman

[57] ABSTRACT

A test system for testing specimens to determine crack propagation utilizing a factor relating to stress intensity at the end of the crack as a control parameter for the loading means.

7 Claims, 6 Drawing Figures

SPECIMEN CRACK STRESS INTENSITY CONTROL LOOP FOR TEST DEVICE

BACKGROUND OF THE INVENTION

1. Field of the Invention

The present invention relates to servo control devices for use in testing tension specimens where crack growth is to be analyzed.

2. Prior Art

Testing of tension specimens to determine crack growth rates has long been carried out. It has been of interest in testing to determine the length of the crack in relationship to load applied and to the number of cycles of operation, and from this information analyze the properties of material from which the specimen is made.

The copending United States Patent Application of William D. Juusola for Test Specimen Crack Correlator, Ser. No. 603,135, filed on even date herewith, discloses means for directly obtaining electrical signals proportional to the crack length of a test specimen. In doing so, a polynomial equation comprising a third order equation that describes the curve of a compliance factor of the specimen plotted versus a quantity comprising the crack length divided by the specimen width is electrically solved.

It has also been recognized in the test field that the stress intensity factor, which describes the severity of stress at the end of the crack in a specimen is a parameter that is of interest in predicting crack growth rates, and otherwise analyzing the effects of loading. The stress intensity factor is used as an independent parameter in formulating fatigue crack growth studies. Previous studies of the influence of stress intensity factor have relied on values that are calculated from load and crack length data after the test. Thus, while recognized as the significant parameter, the stress intensity factor has not heretofore been a parameter that could be usefully used in direct control of tests, or in direct analysis of crack growth.

SUMMARY OF THE INVENTION

The present invention relates to the obtaining and utilization of a signal based on a function of crack length, such as the stress intensity factor of a crack in a tension specimen. The stress intensity factor as shown is provided directly as a function of the compliance of the specimen which is in turn calculated from measured values. The stress intensity factor derived from the disclosed circuitry is used as a feedback to directly control and program the loading of a specimen as a function of the stress intensity in real time. In so doing, the automation of fracture toughness testing is simplified, and the ability to control stress intensity factor by providing a feedback representative of the stress intensity factor and comparing the feedback to a signal representing desired stress intensity enables an investigator to evaluate the dependence of crack growth velocity on various parameters.

The invention includes the use of circuitry for evaluating equations that provide the stress intensity factor. The stress intensity factor is then used to directly control the test program.

DESCRIPTION OF THE PREFERRED EMBODIMENT

Figure 1:
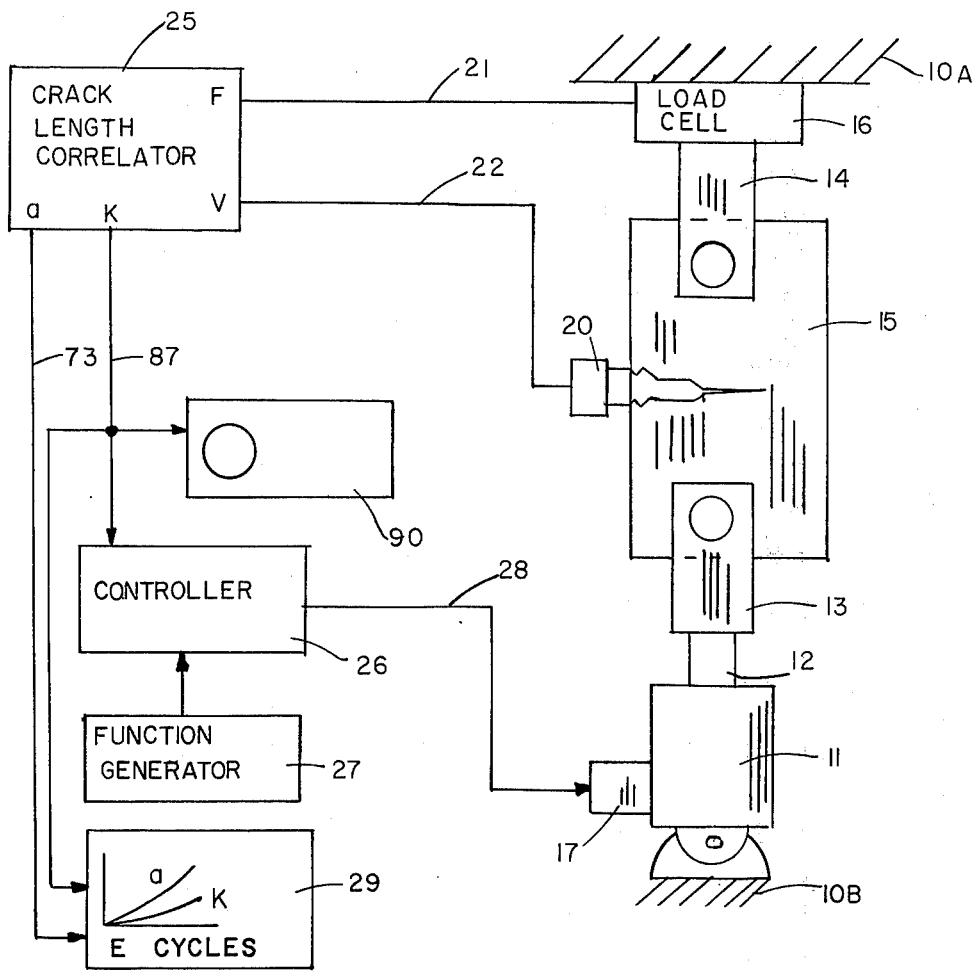
FIG. 1 is a schematic representation of a typical test apparatus controlled in accordance with the present invention.

Referring first to FIG. 1, a simplified schematic representation of a typical servo controlled testing apparatus utlizing a crack growth specimen is shown. A test frame indicated at 10A and 10B is used for mounting an actuator 11 which has a actuable rod 12 acting through a specimen adapter 13 which is fastened to a specimen 15. A load cell 16 is mounted on the second frame portion 10A, and a specimen holder or adapter 14 is further attached to an opposite end of the specimen 15 from the adapter 13.

The specimen 15 as shown is a standard compact tension specimen used for studying crack growth although the use of the device is not limited to only this specimen geometry. The material from which the specimen is made is studied and analyzed. The configuration of the specimen as it is initially made will be explained subsequently, but it is seen that the displacement gage 20 such as an extensometer, is attached to the specimen to measure displacement of the specimen during cyclic loading under operation of the actuator 11.

The actuator is controlled through a servo valve 17 that is operated in a servo control loop. Load signals from the load cell 16 are provided as an analog voltage along line 21, and an indication of displacement of the specimen is provided from the displacement gage 20 as an analog voltage along line 22. The voltage or signal representing load will be represented by the letter F, and the voltage or signal representing the displacement will be represented by the letter V.

The load and displacement signals are provided to a crack length correlator circuit indicated at 25, and a feedback signal will be provided from the crack correlator circuit to a servo controller 26 in the form of the invention shown. As will be more fully explained, the feedback signal in this form of the invention will be a voltage proportional to the stress intensity factor, and a separate function generator 27 can be provided to supply a signal voltage representing the desired stress intensity factor to the controller 26. The output of the function generator will be compared with the feedback signal in the servo controller and a command signal will be provided along the line 28 to the servo valve 17 for controlling the actuator in a manner to obtain the desired stress intensity factor.

In the display of the crack length correlator, the symbol K is used for stress intensity factor, and as will be explained in connection with the discussion of the specimen being tested, the symbol $a$ is representative of crack length.

It should also be noted that the system can include a recorder 29 for recording the information relating to stress intensity factor, crack length, or other desired functions. The horizontal axis shown in the block representing the recorder represents time or cycles, while the vertical axis represents the length of the crack, or the value of the stress intensity factor.

Figure 2:
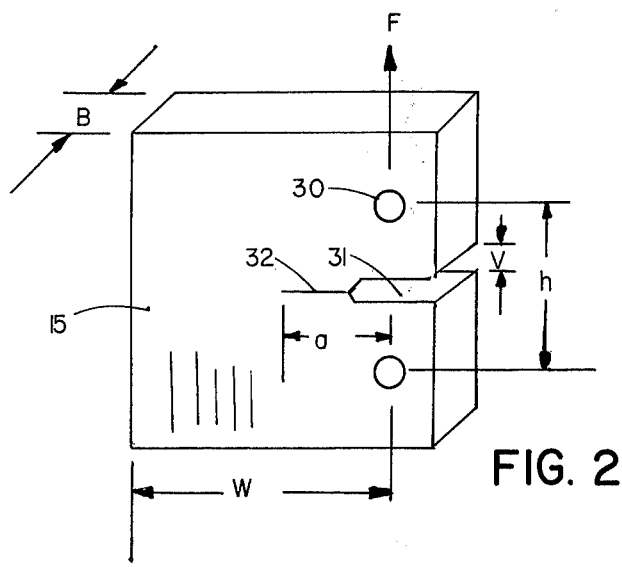
FIG. 2 is a perspective view of a typical specimen utilized in the test device of the present invention.

FIG. 2 shows a typical specimen 15 comprising a compact tension specimen. The specimen 15 has attachment openings 30, 30, and a gap formed in one edge of the specimen indicated at 31. A crack is indicated at 32 and it leads from the inner edge of the gap and grows toward the edge of the specimen opposite from the open end of the gap. In considering the specimen and its features, the width of the specimen is indicated at B; the crack length, as previously mentioned, is $a$, the specimen width is indicated by W; the gap width or displacement of the specimen is represented by V; and the quantity $h$ is the distance between the centers of the attachment openings 30, 30.

Other parameters that are used include the tensile force indicated at F on the FIG. 2, and Young's Modulus will be used and this is designated E in this specification.

Figures 3, 4:
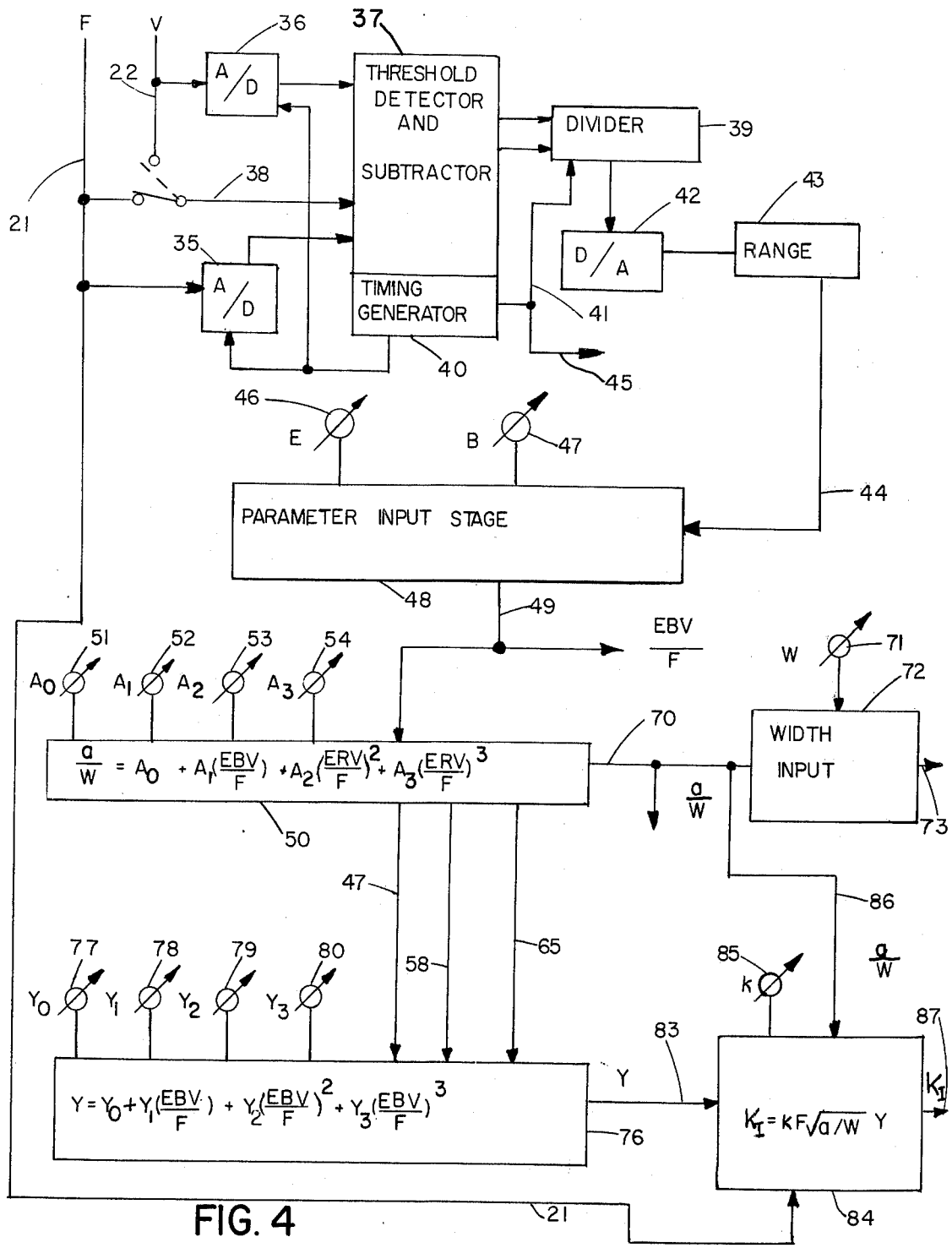
FIG. 3 is a graphical representation of a plot of the function of specimen compliance plotted versus the length of a crack of the specimen divided by its width, and which plot is derived at from empirical or test data and is dependent on the specimen geometry.
FIG. 4 is a further schematic block representation of a crack length correlator represented in FIG. 1.

FIG. 3 shows a plot of quantity EBV/F versus $a$/W, and this curve or plot is approximated by a polynomial equation $$a/W = A_3 \left(\frac{EBV}{F}\right)^3 + A_2 \left(\frac{EBV}{F}\right)^2 + A_1 \left(\frac{EBV}{F}\right) + A_0$$

where the values of $A_0$, $A_1$, $A_2$ and $A_3$ are constants and are unique to the specimen geometry.

A detailed showing of means for obtaining this quantity $a$/W is disclosed in the copending application of William D. Juusola for Test Specimen Crack Correlator, Ser. No. 603,135, filed on even date herewith. A schematic representation of the crack length correlator is disclosed. As stated previously a more detailed representation of the portions of the crack length correlator required to obtain the crack length directly is shown in the aforementioned application of William D. Juusola. Schematically, however, the line 21 carrying the force signal in analog form and the line 22 carrying the displacement signal from displacement gage 20 in analog form are connected to analog to digital converters 35 and 36, respectively, which in turn feed information along data paths to a threshold detector and subtractor indicated at 37. The threshold detector and subtractor is explained more fully in the William D. Juusola application, and is designed so that when a signal along the line 38, which can be connected to either the force or displacement signal lines, exceeds a certain value during each cycle of loading, the value for the appropriate converters is held in a register, and then when the value of the connected signal, for example a load signal, exceeds a certain high threshold the previously held digital values are subtracted from the high threshold values, and these subtracted values are passed into a binary divider 39, and a signal is provided from a timing generator 40 along the line 41 to cause the divider to divide the displacement value by the load, to deliver a quotient that is a binary number to a digital to analog converter 42. The analog output thus is a function of the displacement divided by the load, or V/F. This output is then passed through range selection amplifiers shown generally at 43, along the line 44.

Further, each time the high threshold load is exceeded in each loading cycle, a cycle count pulse is provided along a line 45 so that the number of loading cycles can be used as a time base for recorders and the like.

Fixed parameters such as Young's Modulus (E) and the width of the specimen (B) can be added by variable input controls indicated at 46 and 47, respectively, to the signal on the line 44, and these are normally added through amplifiers which are represented only by a box 48 labeled parameter input stage in the disclosure of FIG. 4. The output signal along the line 49 therefore is proportional to the quantity EBV/F, and is a function of the compliance of the specimen. This signal can be used directly if desired for determining specimen compliance and also is provided into a circuit represented at 50 that provides an electrical output corresponding to $a$/W by solving the equation (1) above as represented in the circuit 50. The constants $A_0$, $A_1$, $A_2$ and $A_3$ are supplied by adjustable controls 51, 52, 53 and 54, respectively. This circuit is shown in detail in the aforementioned application of William D. Juusola and is represented schematically in FIG. 5.

Figure 5:
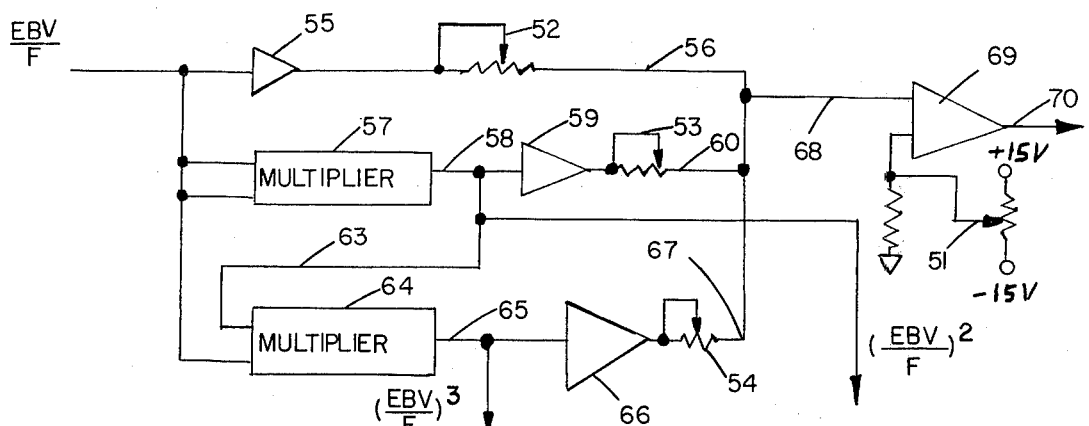
FIG. 5 is a block representation of a portion of the circuitry of FIG. 4.

Referring now to FIG. 5, the EBV/F value, comprising an analog voltage, is connected to the input of a first amplifier 55 and the adjustable resistor or control 52 is on the output so that the quantity $A_1$ (EBV/F) is provided on a line 56. The EBV/F quantity is further supplied to two inputs of a multiplier circuit 57 that provides an output (EBV/F)$^2$ on a line 58, and this signal is provided at the input of an amplifier 59. The adjustable constant $A_3$ is supplied by the adjustable resistor or control 53 at the output of amplifier 59 to provide $A_3$ (EBV/F)$^2$ on line 60. The squared quantity is provided from line 58 along a line 63 to a further multiplier circuit 64 that multiplies the squared quantity times the EBV/F quantity and provides an output signal along the line 65 that is proportional to (EBV/F)$^2$. This quantity is amplified at amplifier 66 and the adjustable resistor or control 54 is connected to the amplifier 66 to provide the constant $A_3$. Line 67 carries a signal proportional to $A_3$ (EBV/F)$^2$. These outputs along the lines 56, 60 and 67 are summed along the line 68 connected to the input of an amplifier 69, which is adjustable through the adjustment device 51 to provide the $A_0$ constant, and provide a signal proportional to $a$/W on a line 70.

Referring again to FIG. 4, quantity W, which is represented by a voltage proportional to the width of the specimen, is provided by an adjustable input 71 to an amplifier circuit 72, and this multiplies the $a$/W quantity by W to provide an output equal to crack length $a$ along a line 73. The output signals EBV/F; (EBV/F)$^2$, and (EBV/F)$^3$ along lines 47, 58 and 65, respectively are provided further to a computational circuit 76, represented in FIG. 4, and the circuit 76 is used to solve for the quantity Y which is derived from a polynomial equation, generally a third order equation. The quantity Y is required for solving for the stress intensity factor. The quantity Y as shown is a function of a third order equation using the specimen compliance factor and adding in different constants, and as represented within the box 76 of FIG. 4. This equation also has previously been known and has been used in hand calculations. The constants $Y_0$, $Y_1$, $Y_2$ and $Y_3$ of the polynomial (third order) equation required for solving for Y are supplied by suitable adjustment devices 77, 78, 79 and 80, respectively which provide inputs to the circuit 76.

The circuit will be more fully explained, but as can be seen the output signal along the line 83, which is proportional to the quantity Y is fed into a computational circuit represented at 84, that solves for the stress intensity factor K by adding in an adjustable constant k through an adjustment device 85, and the load through a line 88, and solving the special case stress intensity factor equation $K_I = kF \sqrt{a/W}\ Y$. The signal representing the quantity a/W comprising crack length divided by specimen width is supplied along the line 86 from the circuit 50 and the resultant stress intensity factor signal $K_I$ for the specimen shown is supplied along the output signal line of the crack length correlator indicated at 87 to the controller 26 and is used as the feedback signal for the controller.

A suitable monitor shown in FIG. 1 and indicated at 90 can be provided for observing the stress intensity factor if desired. Line 87 also is connected to the recorder 29 and line 73 also is shown connected to the recorder. This will give a graphical record of both the stress intensity factor $K_I$ and the crack length $a$.

Figure 6:
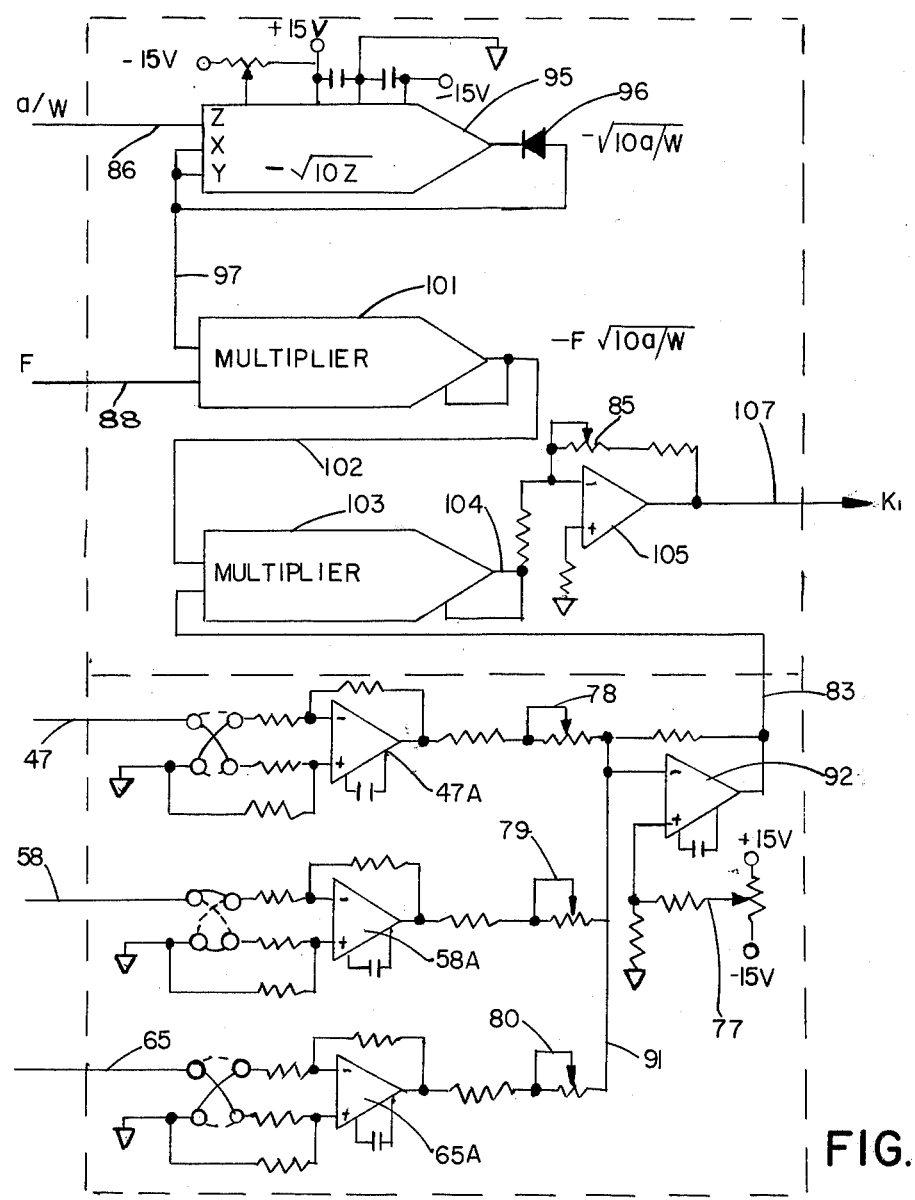
FIG. 6 is a schematic representation of the stress intensity computational circuit illustrated in FIG. 4.

Referring now to FIG. 6, the circuitry utilized for the computational circuits 76 and 84 is illustrated. The circuit 76 is at the lower portion of the figure, and is outlined in dotted lines. The inputs along lines 47, 58 and 65 comprising the quantities EBV/F; $(EBV/F)^2$ and $(EBV/F)^3$ respectively are provided through suitable connections that can be reversed for polarity purposes, to amplifiers 47A, 58A, and 65A, respectively. The outputs of these amplifiers are connected through resistors to provide the constants, including adjustable portions forming adjustable controls 78, 79 and 80 which provide the constants $Y_1$, $Y_2$, and $Y_3$, respectively. The signals are summed along the line 91, and are provided to one input of an amplifier 92. The other input of the amplifier 92 includes the adjustement for the constant $Y_0$ indicated at 77. The output of amplifier 92 provides a signal proportional to the Y quantity along the line 83 as shown in FIG. 6.

The computational circuit 84 is shown in the upper portion of FIG. 6 and also outlined in dotted lines. In the computational circuit 84, a multiplier circuit indicated at 95 comprising a number 4202B circuit made by Burr-Brown Research Corporation of Tucson, Arizona is connected in a known manner to provide an output proportional to minus the square root of 10 times the input value at the Z terminal of the circuit. As can be seen, the signal representing the crack length divided by specimen width (a/W) along line 26 is connected to the Z terminal of the circuit 95, and the normal output of the multiplier circuit is connected through a reversed diode 96 to both the normal X and Y inputs of the amplifier 95. The output in this case is actually derived at the normal inputs of the circuit. This particular multiplier circuit also shows the power supply and balance connections which are specified by the manufacturer. The other multipliers are identical except for the connections. Power connection details will not be shown in connection with the other multiplier circuits.

The output along line 97 is proportional to minus the square root of 10 a/W. All of the 4202B multiplier circuits involve a factor of 10 between the inputs, and the 10 factor is corrected by properly scaled amplifiers. The output signal of line 97 is provided to one input of a multiplier circuit 101. The other input of the multiplier circuit 101 is connected to the load signal line 88, and when a feedback from the output is connected to the Z terminal as shown, the circuit 101 provides an output that is equal to a multiplication of the signals at the input terminals of the circuit 101. The output signal along the line 102 is proportional to $-F \sqrt{10a/W}$.

The signal is provided on line 102 to a further multiplier circuit 103 of the same type, and the input from line 102 is connected to one input of the multiplier circuit while the quantity Y along line 83 from the computational circuit 76 is provided to the other input of the multiplier 103. The output is proportional to these two inputs multiplied by each other. The output of the multiplier 103 along line 104 is connected to one input of an amplifier 105 which provides the necessary gain, and the proper polarity and a potentiometer 85 is used to provide the k factor of the equation represented in the block 84 of FIG. 4. Thus the output along the line 107, comprising the output of the amplifier 105 is the stress intensity factor $K_I$ for this specimen. This quantity can then be provided as shown in FIG. 1 to the controller for the servo system, and the servo system will then be directly controlled as a function of $K_I$.

The values for the resistors utilized to provide the constants depends on specimen geometry, and can be calculated to provide the necessary values. Suitable range selection may be provided to insure the desired output voltage level for servo control.

The power supply used with the circuits (while not shown), provides the necessary excitation voltages for the various amplifiers and multiplier circuits, as well as the logic signal voltages used with the digital portion of the device.

Therefore, the circuit just described provides means for controlling a servo loop on a compact tension test specimen in which crack growth is to be analyzed using stress intensity as the controlling factor and therefore controlling the stress intensity factor at the desired level to study crack growth. The stress intensity factor is a control parameter that previously was unavailable for direct control.

It should be noted that the provision of a signal which is a known function of the crack length is necessary for determining the stress intensity factor. Thus with different values for the constant k the quantity $a$ alone can be used for determining K. The claims are to be interpreted so that the phrase "substantially proportional to crack length" includes the crack length divided by its width.

What is claimed is:
1. A test apparatus for testing tension specimens under cyclic loading, wherein such specimens are caused to crack and crack growth across a width of a specimen is used for a test analysis, the improvement wherein an actuator for loading a specimen to be tested is provided; servo control means for controlling said actuator; means providing a feedback signal substantially proportional to the stress intensity factor at an end of a crack growing in a specimen being tested including transducer means to measure load on a specimen and displacement of a specimen being loaded, means connected to said transducer means to provide a signal proportional to the length of a crack in a specimen being loaded, means to provide a signal which is a function of the compliance of the specimen, multiply- ing circuit means to provide an output signal Y which is substantially proportional to a polynomial function of the compliance factor, and further circuit means to provide an output substantially proportional to the quantity $kF \sqrt{a/W} Y$, where F is a signal proportional to the load applied to the specimen, a is a signal which is a known function of crack length, w is a signal which is a known function of specimen width and k is a constant; and means to couple said output of said further circuit means to said servo control means.

2. A test apparatus for testing tension specimens under cyclic loading, wherein such specimens are caused to crack and crack growth across a width of a specimen is used for a test analysis, the improvement wherein an actuator for loading a specimen to be tested is provided, servo control means for controlling said actuator including first means to provide a signal substantially proportional to the load on a specimen, second means to provide a signal substantially proportional to the displacement of a specimen being loaded, third means connected to said first and second means to provide a signal representing a compliance factor of a specimen being tested based on load and displacement, and means providing a feedback signal substantially proportional to a stress intensity factor of a crack growing in a specimen being tested including fourth means connected to process the signal representing the compliance factor from the third means to provide a signal representing a known function of crack length, fifth means connected to process the signal representing the compliance factor to provide a separate output signal proportional to the value of a polynomial function of the signal representing the compliance factor, and sixth means to provide an output which is substantially proportional to the load signal, the square root of the signal from the fourth means and the separate output signal of the fifth means and means to couple the output signal from the sixth means to the servo control means.

3. The apparatus of claim 2 wherein said third means to provide a signal representing a compliance factor of a specimen being tested provides a signal substantially proportional to (EBV)/F where V/F represents load divided by force, E is Young's modulus for the material of a specimen being loaded and B is the thickness of a specimen being loaded.

4. The apparatus as specified in claim 3 wherein said fifth means provides an output signal proportional to Y where $$Y = Y_1 + Y_2 \left(\frac{EBV}{F}\right) + Y_2 \left(\frac{EBV}{F}\right)^2 + Y_3 \left(\frac{EBV}{F}\right)^3$$

where $EBV/F$ represents the compliance factor and $Y_0$, $Y_1$, $Y_2$ and $Y_3$ are constants.

5. A test apparatus for testing tension specimens under cyclic loading, wherein such specimens are caused to crack and crack growth is used for a test analysis, an actuator to load a specimen, servo control means for controlling said actuator, first means to provide signals representing load on and displacement of a specimen being loaded, second means to provide a signal representing a compliance factor based on load and displacement characteristics, and third means to provide a signal substantially proportional to crack length as a function of said compliance factor, the improvement comprising fourth means coupled to the second means to receive said signal representing said compliance factor and to provide a selected output signal based on a polynomial function of said compliance factor; and fifth means connected to said first means to receive said load signal, and connected to said third means to receive said signal substantially proportional to crack length and connected to said fourth means to receive said output signal based on the polynomial function of the compliance factor, said fifth means combining the load signal from said first means and the signals from the third and fourth means to provide a feedback signal substantially proportional to the stress intensity factor of a crack growing in a specimen being tested, and means to connect the fifth means to said servo control means.

6. The combination of claim 5 wherein said selected output signal from the second means is represented by the quantity i based on a third order of said compliance factor is represented by the quantity Y, and wherein said fifth means connected provides an output feedback signal substantially proportional to the quantity $kF \sqrt{a/W} Y$, where F is the signal proportional to the load applied to the specimen, $a$ is a quantity substantially proportional to crack length, W is a quantity substantially proportional to specimen width, $a/W$ is a signal which is a function of crack length, and k is a constant.

7. A method of controlling a test apparatus for testing a specimen having a specimen width in which crack growth across the specimen width is to be analyzed, and having an actuator for loading said specimen in a cyclic load, including the steps of determining a specimen compliance factor which is a function of load applied in relation to displacement of a loaded specimen, providing a signal proportional to crack length, and providing a polynomial function signal representing a stress intensity factor by combining signals representing said compliance factor, the load applied to the specimen, and a signal substantially proportional to the square root of said signal which is substantially proportional to crack length, and using the stress intensity factor signal as a feedback signal for controlling the actuator in a closed loop control.

* * * * *